US009962279B2

(12) United States Patent
Haley et al.

(10) Patent No.: US 9,962,279 B2
(45) Date of Patent: May 8, 2018

(54) ANKLE-FOOT ORTHOTIC BOOT

(71) Applicant: Desiree Spring Haley, Gregory, MI (US)

(72) Inventors: Desiree Spring Haley, Gregory, MI (US); Kyle Thomas Balancio Lee, Shelby Township, MI (US); Kara Maureen Miller, Grosse Ile, MI (US); Danika Jho Rodrigues, Novi, MI (US); Spencer Scott Paris, Gwinn, MI (US)

(73) Assignee: Desiree Spring Haley, Gregory, MI (US)

( * ) Notice: Subject to any disclaimer, the term of this patent is extended or adjusted under 35 U.S.C. 154(b) by 220 days.

(21) Appl. No.: 15/072,310

(22) Filed: Mar. 16, 2016

(65) Prior Publication Data
US 2016/0270943 A1 Sep. 22, 2016

Related U.S. Application Data

(60) Provisional application No. 62/133,582, filed on Mar. 16, 2015.

(51) Int. Cl.
A61F 5/01 (2006.01)
A43B 7/20 (2006.01)

(52) U.S. Cl.
CPC .............. A61F 5/0127 (2013.01); A43B 7/20 (2013.01); A61F 5/0113 (2013.01); A61F 2005/0137 (2013.01)

(58) Field of Classification Search
CPC .................. A61F 5/0113; A61F 5/0127; A61F 2005/0137; A43B 7/20
See application file for complete search history.

(56) References Cited

U.S. PATENT DOCUMENTS

| 4,289,122 A | 9/1981 | Mason |
| 4,554,912 A | 11/1985 | Haberman |
| 5,078,128 A * | 1/1992 | Grim ............... A61F 5/0127 602/23 |
| 5,125,171 A * | 6/1992 | Stewart ............. A43B 5/00 36/114 |
| 5,486,157 A | 1/1996 | DiBenedetto |
| 7,125,392 B2 | 10/2006 | Scott |
| 8,075,633 B2 | 12/2011 | Herr |
| 8,114,042 B2 | 2/2012 | Klotz |
| 8,287,477 B1 | 10/2012 | Herr |

(Continued)

OTHER PUBLICATIONS http://lermagazine.com/issues/may/allard-usa-get-back-up-today, last visited Mar. 16, 2016.

(Continued)

Primary Examiner — Daniel J Colilla
(74) Attorney, Agent, or Firm — Diana D. Brehob

(57) ABSTRACT

Ankle-foot orthotics are used by many people suffering from foot drop. Some are applied to the foot and then inserted into standard footwear. They present many disadvantages. Alternatively, the orthotic is external causing extra attention to the orthotic. Disclosed herein is an ankle-foot orthotic (AFO) that is integrated into a boot. The AFO is less obvious and the boot material is in contact with the wearer's foot rather than the orthotic itself. A calf plate hinged with a sole plate are inserted into the shoe, as well as a member in tension biasing the foot toward dorsiflexion.

19 Claims, 4 Drawing Sheets

(56) References Cited

U.S. PATENT DOCUMENTS

| | | | |
|---|---|---|---|
| 8,376,971 B1 | 2/2013 | Herr | |
| 8,382,694 B2 | 2/2013 | Wenger | |
| 8,480,546 B2* | 7/2013 | Spencer | A43B 7/00 |
| | | | 482/44 |
| 2002/0035344 A1* | 3/2002 | Herzberg | A61F 5/0111 |
| | | | 602/41 |
| 2005/0038365 A1 | 2/2005 | Scott | |
| 2005/0070834 A1 | 3/2005 | Herr | |
| 2010/0324465 A1 | 12/2010 | Klotz | |
| 2011/0082404 A1 | 4/2011 | Wenger | |
| 2012/0136459 A1 | 5/2012 | Herr | |
| 2013/0138030 A1 | 5/2013 | Wenger | |
| 2016/0058595 A1* | 3/2016 | Tsitouras | A61F 5/0113 |
| | | | 602/28 |
| 2016/0278961 A1* | 9/2016 | Sutti | A61F 5/0111 |

OTHER PUBLICATIONS http://www.acor.com/KeepingPaceFootwear.php, last visited Mar. 16, 2016.

http://www.ossur.com/injury-solutions/products/foot-and-ankle/ankle-foot-orthosis/foot-up, last visited Mar. 16, 2016.

http://www.ottobockus.com/orthotics/solution-overview/ankle-brace-walkon/, last visited Mar. 16, 2016.

http://www.docortho.com/swede-o-step-smart.html?utm_source=msn&utm_medium=cpc&utm_campaign=%28roi%29+swede-o&utm_content=step+smart&utm_term=%2Bstep%20%2Bsmart&utm_creative=e&utm_device=c&promo=control, last visited Mar. 16, 2016.

http://www.braceshop.com/ossur-afo-light-drop-foot-brace.htm?utm_source=BingShopping&utm_medium=shopping&utm_campaign=Ossur%20Braces&origin=bpa&unique_id=28150&gdftrk=gdfV28018_a_7c2568_a_7c11941_a_7c28150, last visited Mar. 16, 2016.

http://walkaide.com/Pages/default.aspx, last visited Mar. 16, 2016.

http://lermagazine.com/cover_story/biomechanics-of-propulsion-implications-for-afos, last visited Mar. 16, 2016.

http://lermagazine.com/article/controlling-drop-foot-beyond-standard-afos, last visited Mar. 16, 2016.

* cited by examiner

ANKLE-FOOT ORTHOTIC BOOT

FIELD

The disclosure relates to an ankle-foot orthotic, in particular for the treatment of drop foot.

BACKGROUND

Approximately 6,000,000 orthotic devices are sold annually in the U.S. to the many people, including one of the inventors of the present application, suffer from drop foot, a neural disorder in which one cannot dorsiflex, or raise up, the toes or raise the foot from the ankle. As a result, the foot is stuck in a plantar flexed (hanging) position and drags on the ground when walking. This condition can be caused by: stroke, ALS, muscular dystrophy, multiple sclerosis, cerebral palsy, bone sarcoma, and aplastic paraplegia.

A person with drop foot may employ one or more of the following strategies while walking to avoid the foot from dragging on the ground: bending the knee of the affected leg, lifting the hip to swing the leg forward, and swinging the leg outward. Such gaits result in fatigue, misalignment of the spine and neck, and increased falling incidents, as well as calling unwanted attention to the person with such a gait.

Persons suffering from drop foot commonly suffer from neuropathy, a pins-and-needles sensation along with hypersensitivity to modest stimuli, such as the rubbing associated with donning a shoe.

Many people with drop foot wear an ankle-foot orthotic (AFO) to provide a more natural gait. Prior art AFOs are strapped to the leg and then inserted into a shoe to physically manipulate the ankle to dorsiflex. Because the AFO is bulky, users buy a shoe of a size larger than they would normally wear without the orthotic. If only one of the patient's feet has drop foot, two pairs of shoes are purchased, one for the foot wearing the orthotic and the normal size for the unaffected foot. The AFO interferes with typical shoes in one or more spots which necessitate cutting the shoe back to make it fit. A custom orthotic costs in excess of $1000, lasts from 6 months to 3 years, causes many wearers to buy 2 pairs of shoes to accommodate the AFO on one foot, and the shoe into which the AFO is fitted is further compromised by cutting it back, thereby reducing the normal life of the shoe and further making the wearer's condition more conspicuous. This represents a significant cost to AFO wearers with a limited period of satisfactory performance of their shoe/orthotic system.

Depending on the condition and the severity that leads to drop foot, many of those suffering from it are unable to self-dress, particularly to reach the end of an extremity like the leg to pull on a shoe. Adding the complication of putting a foot with an orthotic attached into a shoe exacerbates the situation. Having an AFO that allows such persons to dress independently is a desirable goal.

For AFO wearers suffering from neuropathy, having AFO pushing against the foot to cause the foot to move in a desired way causes rubbing with the foot. There is some rubbing between foot and shoe while walking for anyone. However, with an AFO attached to one's leg(s) and that AFO having hard surface can lead to excruciating pain for some.

Another problem with the state of the art is that people who suffer from drop foot have difficulty sliding their foot into a shoe. The toes curl under and difficult to uncurl. Some people with neuropathy may not notice until they experience pain while walking.

SUMMARY

To overcome at least one problem in the prior art, an AFO integrated into a boot is disclosed. An ankle-foot orthotic (AFO) boot includes: a sole and a sole plate having a vertical portion and a horizontal portion. An upper end of the vertical portion has a tab extending upwardly with an orifice defined through the tab. The AFO boot further includes a calf plate having an upper portion that is substantially half of a cylinder and a lower portion that has a tab extending downwardly with an orifice defined through the tab, a pin of rotation extending into the orifice in the tab of the sole plate and into the orifice in the tab of the calf plate, a member in tension coupled between the upper portion of the calf plate and the sole, a boot upper affixed to the sole, the boot upper having pockets therein to accommodate the calf plate and the sole plate, and a first fastener portion coupled to a first side of the boot upper and a second fastener portion coupled to a second side of the boot upper. The first and second fastener portions are located proximate the upper portion of the calf plate.

The AFO boot may further include a pin of affixment extending into the sole and a cylinder integrated into the upper portion of the calf plate. The member in tension includes a spring disposed in the cylinder and a slender cable affixed to the spring at a first end and affixed to the pin of affixment at a second end.

The member coupled between the upper portion of the calf plate and the sole is a first member, in some embodiments, the AFO boot also has a second member coupled between the upper portion of the calf plate and the sole. The first member is coupled to a first side of the sole and the second member is coupled to a second side of the sole; and the first side is opposite the second side.

A casing may be provided in the boot upper for the member in tension to encase the member in tension, a cable portion of the member in tension.

The first fastener portion, in some embodiments, is a hook portion of a hook-and-loop tape and the second fastener is a loop portion of the hook-and-loop tape. Alternatively, the fasters are a buckle and tab or any suitable fastener system.

The AFO boot further includes a third fastener portion coupled to the first side of the boot upper and a fourth fastener portion coupled to a second side of the boot upper. The third and fourth fastener portions are located proximate the sole.

A first of the pockets is closed after the calf plate is inserted therein to thereby prevent the calf plate from coming out of the first of the pockets.

The boot upper comprises at least a first side, a second side, and a tongue. The tongue is coupled to the sole at a toe portion of the sole distal from the sole plate. The tongue is attached to the first side and the second side to allow the tongue to be folded away from the sole plate to provide a substantially unobstructed vertical entrance for a foot. In an alternative embodiment, the tongue is applied to the first side of the boot upper and folds to the side to provide the substantially unobstructed vertical entrance for a foot.

The first and second fastener portions are arranged on the first and second sides so that the first fastener portion and the second fastener portion secure the tongue when fastened.

An AFO boot is disclosed that includes a sole having a heel end and a toe end, a boot upper coupled to the sole, two members in tension with one end of each of the members coupled to the sole at a location closer to the toe end of the sole than the heel end and one end of each of the members coupled to a portion of the boot upper distal from the sole.

Two casings are provided in the boot upper with one of the members in tension threaded through each of the casings.

The AFO boot further includes a sole plate having a vertical portion and a horizontal portion wherein an upper end of the vertical portion has tab extending upwardly with an orifice defined through the tab, a calf plate having an upper portion that is substantially half of a cylinder and a lower portion that has a tab extending downwardly with an orifice defined through the tab, and a pin of rotation extending into the orifice in the tab of the sole plate and into the orifice in the tab of the calf plate.

The AFO boot has a first fastener portion coupled to a first side of the boot upper and a second fastener portion coupled to a second side of the boot upper. The first and second fastener portions are located proximate the upper portion of the calf plate.

The first and second fastener portions are one of: a buckle system and a loop-and-pile closure system.

The boot upper has at least a first side, a second side, and a tongue. The tongue is coupled to the sole at a toe portion of the sole distal from the sole plate. The tongue is attached to the first side and the second side of the boot upper so as to allow the tongue to be folded away from the sole plate to provide a substantially unobstructed vertical entrance of a foot into the boot.

In some embody embodiment, an insole placed inside the boot, over the sole.

The boot upper is coupled to the sole. The boot upper has pockets therein to accommodate the calf plate and the sole plate.

Also disclosed is a method to assemble an ankle-foot orthotic boot, including: cutting and forming a boot upper, forming a pocket in the boot upper, manufacturing a calf plate, inserting the calf plate into the pocket in the boot upper, manufacturing a sole, affixing the sole to the boot upper, and attaching a member in tension between the calf plate and the sole.

The method may further include manufacturing a sole plate that has a vertical portion and a horizontal portion with an upper end of the vertical portion having a tab extending upwardly and an orifice defined through the tab; and placing a pin of rotation through the orifice in the tab of the sole plate and through the orifice in the tab of the calf plate.

The boot upper has a first side, a second side and a tongue between the first and second side. The method further includes providing a first fastener portion on the first side of the boot upper and providing a second fastener portion on the second side of the boot upper wherein the first and second fasters secure the tongue when fastened.

By integrating the orthotic into a boot, donning the footwear is simplified. Furthermore, instead of having a hard plastic orthotic rubbing against the foot, the disclosed AFO boot has fabric or other lining material touching the foot. The issues with putting the orthotic into a shoe: buying 2 sizes and cutting back the shoe are eliminated by an integrated AFO boot. By providing a tongue that folds back (or to the side), entry of the foot into the AFO boot is greatly eased to avoid toe curling.

DETAILED DESCRIPTION

As those of ordinary skill in the art will understand, various features of the embodiments illustrated and described with reference to any one of the Figures may be combined with features illustrated in one or more other Figures to produce alternative embodiments that are not explicitly illustrated or described. The combinations of features illustrated provide representative embodiments for typical applications. However, various combinations and modifications of the features consistent with the teachings of the present disclosure may be desired for particular applications or implementations. Those of ordinary skill in the art may recognize similar applications or implementations whether or not explicitly described or illustrated.

Figure 1:
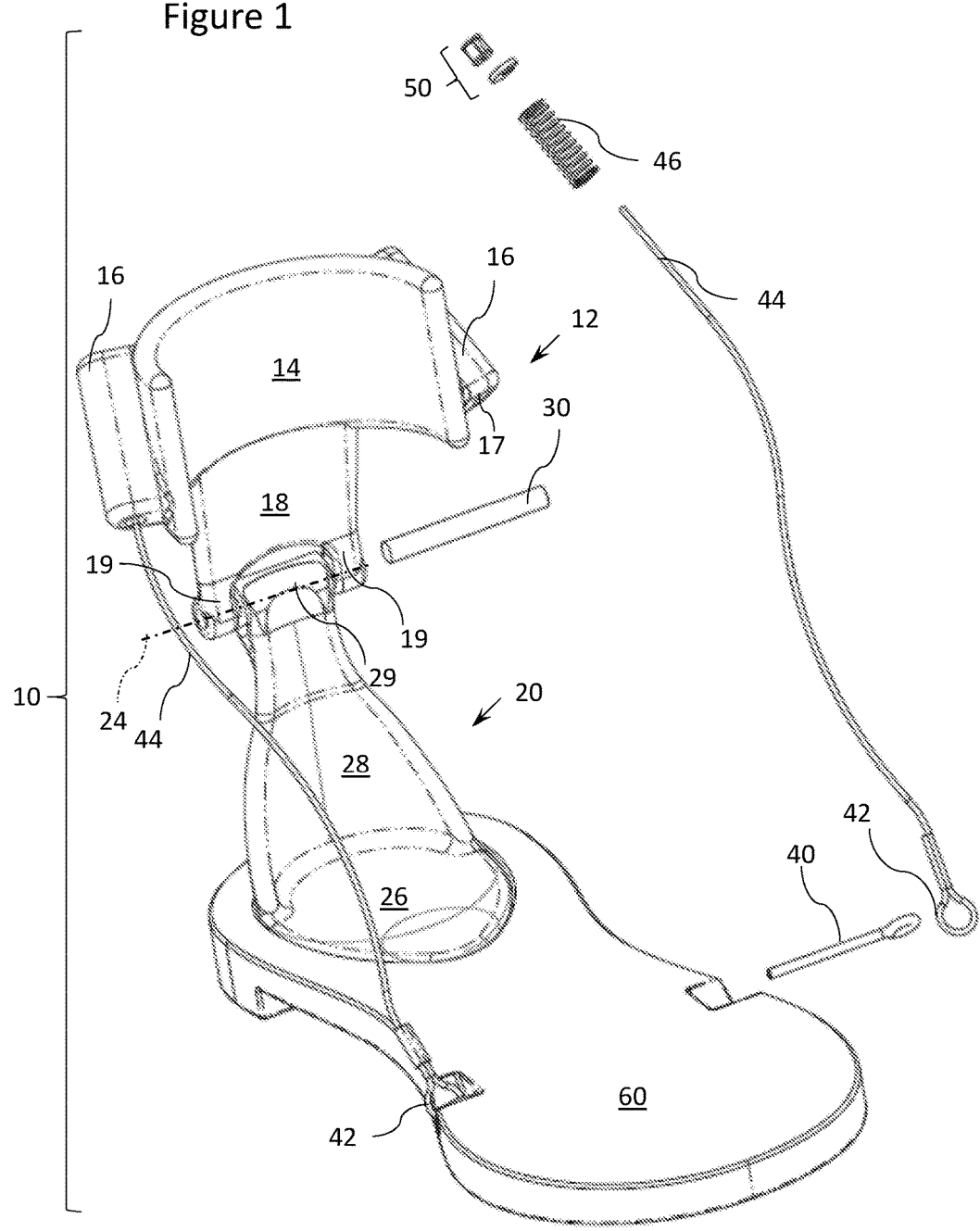
FIGS. 1, 2, and 3 show an isometric view partially exploded, a transparent isometric view, and a side view, respectively of an ankle-foot orthotic that can be integrated into a boot.

A partially exploded view of the operational portion 10 of an AFO that can be integrated into a boot is shown in FIG. 1. A calf plate 12 has an upper portion 14 that is shaped substantially like a portion of a cylinder with the inner, concave surface adapted to fit around an ankle and the outer, convex surface having two attachment cylinders 16 coupled thereto. A lower portion 18 of calf plate 12 has tabs 19 that extend downward from calf plate 12. Tabs 19 have an orifice defined therethrough, which is denoted by centerline 24.

A sole plate 20 has a vertical section 28 and a horizontal section 26. A tab 29 extends upwardly from vertical section 28 and has an orifice defined therethrough that is coincident with centerline 24. A pin 30 is inserted into the orifices in tabs 19 and 29 to allow calf plate to rotate around centerline 24 with respect to sole plate 26. Horizontal section 26 of sole plate 20 sits into a depression in a sole 60.

A member in tension is provided between upper portion 14 of calf plate and sole 60. In the embodiment in FIG. 1, a pin 40 with a loop at one end is inserted into sole 60. A thin cable 42 with a loop at one end can engage with the loop of pin 40. The end of cable 42 distal from the loop can be secured to a spring 46 via fastening system 50. In some embodiments, pin 40 couples to another pin on the other side coupling in the center. In an alternative embodiment, a single pin traverses through sole 60 and attaches to cable 44 in any suitable fashion.

In some embodiments, cable 42 is stretchy and provides the desired tension. In such a case, cable 42 may be directly coupled to upper portion 14 without attachment cylinders 16.

Figure 2:
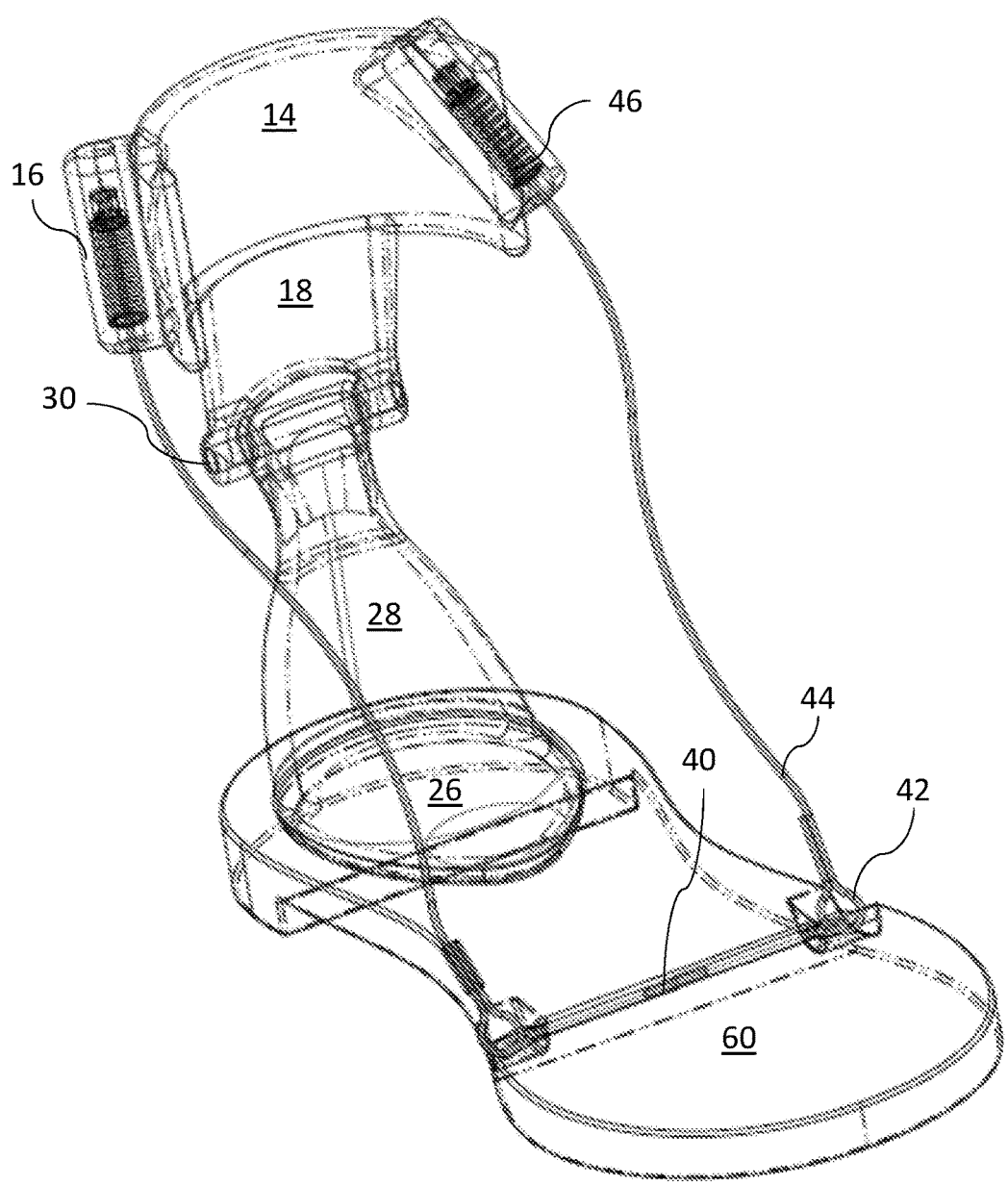
Figure 3:
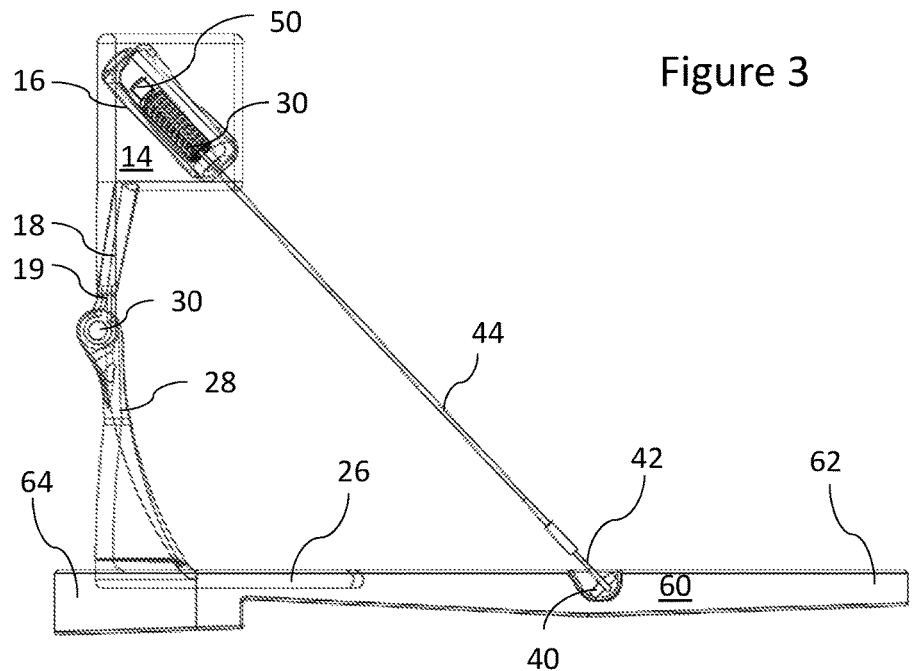

In FIG. 2, a transparent view of the AFO portion of the boot is shown. Referring now to FIG. 3, a side view is shown. A toe portion 62 is at one end of sole 60 and a heel portion 64 is at the other end.

Figure 4:
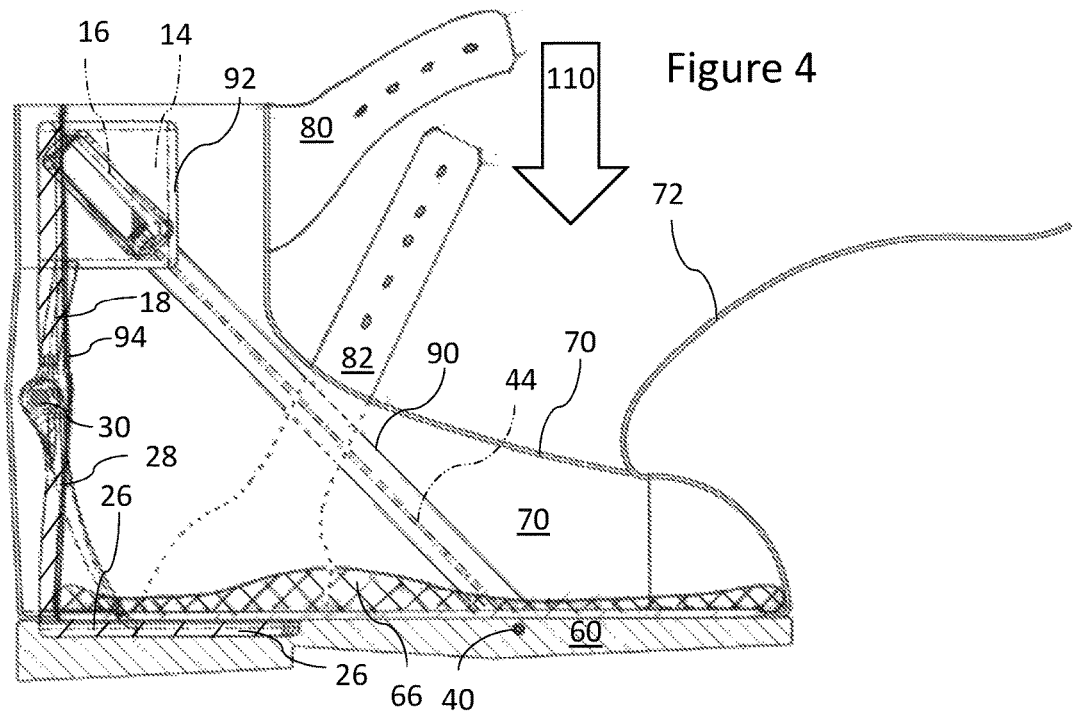
FIG. 4 is a cross-sectional view of an ankle-foot orthotic boot.

In FIG. 4, a boot with an integrated AFO is shown in cross section. The AFO components have been described in regard to FIG. 1 and are not separately described here. The boot has a boot upper, the part that in typical shoes is made out of canvas, leather, or synthetic material. The boot upper is made of several parts including a first side 70, a second side (not shown as this is a cross sectional view), a tongue 72, and fasteners. A fastener portion 80 is a tab that has hole in it. A complementary fastener portion (not shown because the view is in cross section) has a buckle with a post that engages with one of the holes in fastener portion 80. A similar arrangement is contemplated for a fastener portion 82 that is also provided on first side 70 of the boot upper. In an alternative embodiment, fastener portions 80 and 82 are provided with the loop or pile tape of a Velcro fastener and the complementary fastener portions that are not visible in FIG. 4 have the other of the loop and pile tape applied. Any suitable fastener system can alternatively be employed. Also, additional fastener pairs can be provided to increase foot security.

By providing a tongue 72 that is minimally coupled to the sides of the boot upper, it can be folded out of the way of the shoe opening a foot can be put into the boot substantially vertically, as indicated by arrow 110. After the foot is installed into the boot, tongue 72 is placed over the foot and the fasteners are deployed to secure the foot in that boot. As described above, in an alternative embodiment, tongue 72 is affixed to left side 70 of the boot upper and can be folded to the left to allow easy donning of the boot. (Tongue 72 could be affixed, alternatively to the right side of the boot.)

A casing 90 is provided in left side 70 of the boot upper to encase cable 44. Alternatively, casing 90 encases only part of cable 44 to provide a guide for cable 44, but more flexibility in adjusting to the movement of the foot. Pockets 92 and 94 are sewn into boot upper to encase the calf plate (includes elements 14, 16, and 18). A pocket may also be provided for an upper portion of the sole plate.

An insole 66 is provided into the AFO boot. Insole 66 covers sole 60 and in some embodiments covers horizontal section 26 of the sole plate.

Figure 5:
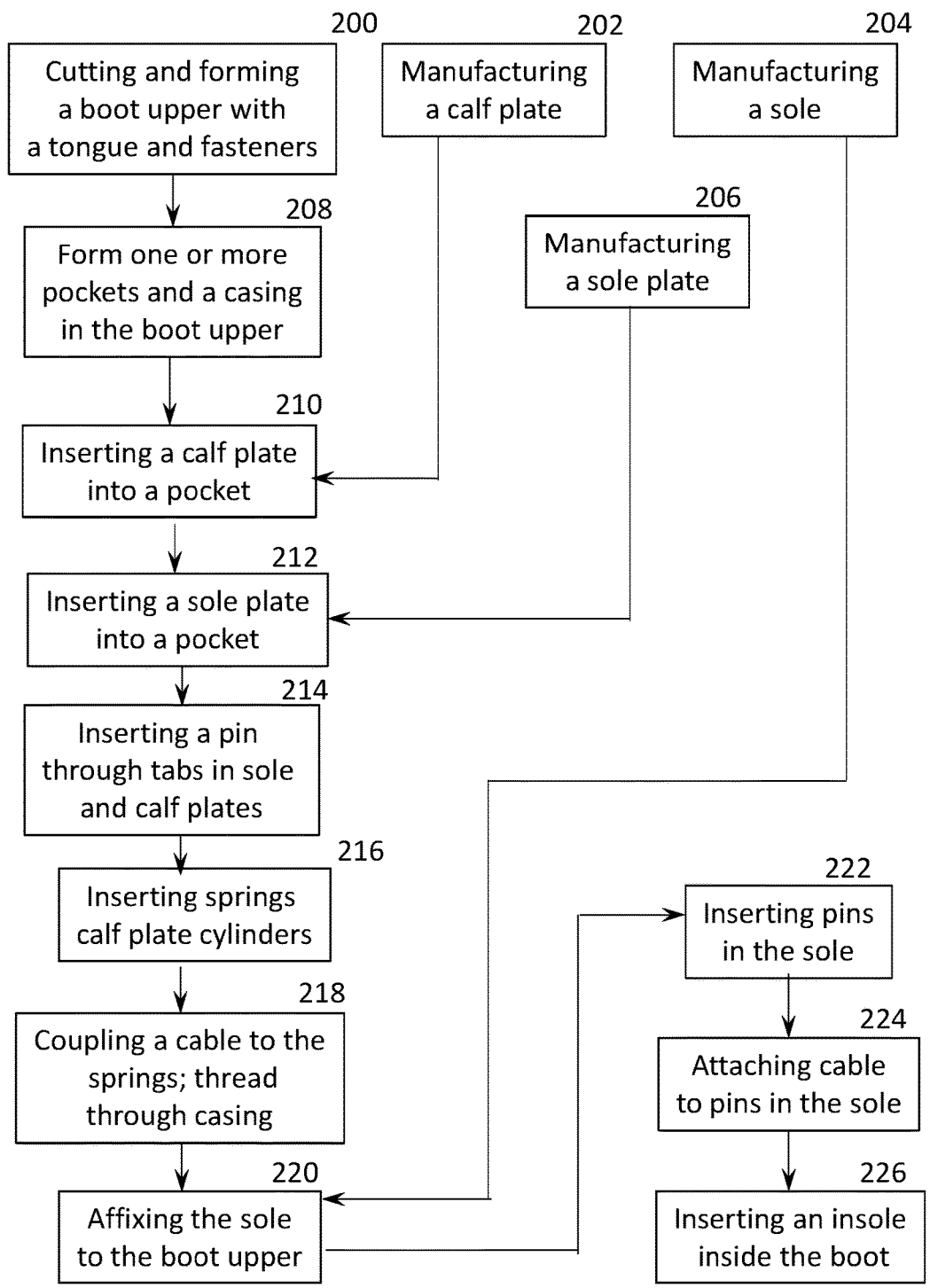
FIG. 5 is a flow chart describing a process for assembling an AFO boot.

A process for making such an AFO boot is shown in FIG. 5. The order of the processes may be varied in alternative embodiments or some processes eliminated or replaced. A boot upper is cut and formed including the two sides, the tongue, fasteners, and any other pieces in block 200. In block 208 any pockets for the orthotics components are provided. In block 202, a calf plate is formed by: injection molding, 3D printing, or any suitable process. The calf plate is inserted into one of the pockets specially made for it, in bloc, 210. A sole plate is manufactured in block 206 and inserted into a pocket in the boot upper in block 212. In block 214, a pin is inserted in the tabs of the sole plate and the calf plate to provide a hinge at that point. The member in tension is, in some embodiments, a spring and a cable. The springs are inserted into cylinders provided in the calf plate in block 216. The cable is coupled to the springs and threaded through the casings provided in the boot upper in block 218. In block 204, a sole is manufactured and then affixed to the boot upper in block 220. Pins are inserted into the sides of the sole in block 222. These pins are provided as an attachment point for the cable as described in block 224. An insole is provided in the boot in block 226.

While the best mode has been described in detail with respect to particular embodiments, those familiar with the art will recognize various alternative designs and embodiments within the scope of the following claims. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. The embodiments described herein that are characterized as less desirable than other embodiments or prior art implementations with respect to one or more characteristics are not outside the scope of the disclosure and may be desirable for particular applications.

We claim:
1. An ankle-foot orthotic (AFO) boot, comprising:
a sole;
a sole plate having a vertical portion and a horizontal portion wherein an upper end of the vertical portion has a tab extending upwardly with an orifice defined through the tab;
a calf plate having an upper portion that is substantially half of a cylinder and a lower portion that has a tab extending downwardly with an orifice defined through the tab;
a pin of rotation extending into the orifice in the tab of the sole plate and into the orifice in the tab of the calf plate;
a member in tension coupled between the upper portion of the calf plate and the sole;
a boot upper affixed to the sole, the boot upper having pockets therein to accommodate the calf plate and a portion of the sole plate; and
a first fastener portion coupled to a first side of the boot upper and a second fastener portion coupled to a second side of the boot upper, the first and second fastener portions located proximate the upper portion of the calf plate.

2. The AFO boot of claim 1, further comprising:
a pin of affixment extending into the sole; and
a cylinder integrated into the upper portion of the calf plate wherein the member in tension comprises:
a spring disposed in the cylinder; and
a slender cable affixed to the spring at a first end and affixed to the pin of affixment at a second end.

3. The AFO boot of claim 1 wherein the member coupled between the upper portion of the calf plate and the sole is a first member, the AFO boot further comprising:
a second member coupled between the upper portion of the calf plate and the sole wherein the first member is coupled to a first side of the sole and the second member is coupled to a second side of the sole; and the first side is opposite the second side.

4. The AFO boot of claim 1 wherein a casing is defined in the boot upper and the member in tension is threaded through the casing.

5. The AFO boot of claim 1 wherein the first fastener portion comprises a hook portion of a hook-and-loop tape and the second fastener comprises a loop portion of the hook-and-loop tape.

6. The AFO boot of claim 1, further comprising:
a third fastener portion coupled to the first side of the boot upper; and
a fourth fastener portion coupled to a second side of the boot upper wherein the third and fourth fastener portions are located proximate the sole.

7. The AFO boot of claim 1 wherein a first of the pockets is closed after the calf plate is inserted therein to thereby prevent the calf plate from coming out of the first of the pockets.

8. The AFO boot of claim 1 wherein:
the boot upper comprises at least a first side, a second side, and a tongue;
the tongue is coupled to one of the sole, the first side, and the second side; and
the tongue is attached to the first side and the second side to allow the tongue to be folded back to provide a substantially unobstructed vertical entrance of a foot.

9. The AFO boot of claim 8, further comprising:
a first fastener portion coupled to the first side; and
a second fastener portion coupled to the second side wherein the first and second fastener portions are arranged on the first and second sides such that the first fastener portion and the second fastener portion to secure the tongue when fastened.

10. An ankle-foot orthotic (AFO) boot, comprising:
a sole having a heel end and a toe end;
a boot upper coupled to the sole;
two members in tension with one end of each of the members coupled to the sole at a location closer to the toe end of the sole than the heel end and one end of each of the members coupled to a portion of the boot upper distal from the sole wherein two casings are provided in the boot upper with one of the two members in tension threaded through each of the casings;
a sole plate having a vertical portion and a horizontal portion wherein an upper end of the vertical portion has a tab extending upwardly with an orifice defined through the tab;
a calf plate having an upper portion that is substantially half of a cylinder and a lower portion that has a tab extending downwardly with an orifice defined through the tab; and
a pin of rotation extending into the orifice in the tab of the sole plate and into the orifice in the tab of the calf plate.

11. The AFO boot of claim 10, further comprising:
a first fastener portion coupled to a first side of the boot upper; and
a second fastener portion coupled to a second side of the boot upper wherein the first and second fastener portions are located proximate the upper portion of the calf plate.

12. The AFO boot of claim 11 wherein the first and second fastener portions comprise one of: a buckle system and a loop-and-pile closure system.

13. The AFO boot of claim 10 wherein:
the boot upper comprises at least a first side, a second side, and a tongue;
the tongue is coupled to one of the first side, the second side and the sole; and
the tongue is attached so as to allow the tongue to be folded away from the sole to provide a substantially unobstructed vertical entrance of a foot into the boot, the AFO boot further comprising:
an insole placed inside the AFO boot over the sole.

14. The AFO boot of claim 10 wherein the boot upper is coupled to the sole; and the boot upper has pockets therein to accommodate the calf plate.

15. The AFO boot of claim 10
wherein a first of the two members in tension is coupled to a first side of the sole; a second of the two members in tension is coupled to a second side of the sole; and the first side is opposite the second side.

16. A method to assemble an ankle-foot orthotic boot, comprising:
cutting and forming a boot upper;
forming a pocket in the boot upper;
manufacturing a calf plate;
inserting the calf plate into the pocket in the boot upper;
manufacturing a sole;
affixing the sole to the boot upper; and
attaching a member in tension between the calf plate and the sole.

17. The method of claim 16 wherein the calf plate has an upper portion that is substantially half of a cylinder and a lower portion that has a tab extending downwardly with an orifice defined through the tab, the method further comprising:
manufacturing a sole plate that has a vertical portion and a horizontal portion with an upper end of the vertical portion having a tab extending upwardly and an orifice defined through the tab; and
placing a pin of rotation through the orifice in the tab of the sole plate and through the orifice in the tab of the calf plate.

18. The method of claim 16 wherein the boot upper has a first side, a second side and a tongue between the first and second side, the method further including:
providing a first fastener portion on the first side of the boot upper; and
providing a second fastener portion on the second side of the boot upper wherein the first and second fasters secure the tongue when fastened.

19. The method of claim 18, further comprising: placing an insole onto the sole and a horizontal portion of the sole plate.

* * * * *